United States Patent [19]
Marsoner et al.

[11] Patent Number: 5,074,157
[45] Date of Patent: Dec. 24, 1991

[54] ANALYZING APPARATUS

[75] Inventors: Hermann Marsoner, Steinberg; Helmut List, Graz, both of Austria

[73] Assignee: AVL AG, Schaffhausen, Switzerland

[21] Appl. No.: 488,532

[22] Filed: Feb. 28, 1990

Related U.S. Application Data

[63] Continuation of Ser. No. 209,370, Jun. 21, 1988, abandoned.

[30] Foreign Application Priority Data

Jun. 30, 1987 [AT] Austria .................................. 1648/87

[51] Int. Cl.$^5$ ............................................. G01N 1/00
[52] U.S. Cl. ..................................... 73/864.81; 204/409
[58] Field of Search ........... 73/864.21, 864.87, 864.81; 128/635; 204/403, 409–412, 416, 422, 228–231, 250, 267–269, 274, 275; 324/450, 438

[56] References Cited

U.S. PATENT DOCUMENTS

| | | | |
|---|---|---|---|
| 3,763,422 | 10/1973 | MacPhee et al. | 324/438 |
| 3,824,168 | 7/1974 | Oswin et al. | 204/411 |
| 3,853,732 | 12/1974 | Brand et al. | 204/409 |
| 3,884,640 | 5/1975 | Lock et al. | 324/438 |
| 3,997,420 | 12/1976 | Buzza | 204/411 |
| 4,202,747 | 5/1980 | Buzza et al. | 204/411 |
| 4,552,013 | 11/1985 | Matson | 204/411 |
| 4,627,893 | 12/1986 | Cormier et al. | 204/411 |
| 4,700,709 | 10/1987 | Kraig | 128/635 |
| 4,713,618 | 12/1987 | Carlson et al. | 324/438 |
| 4,717,548 | 1/1988 | Lee | 128/635 |
| 4,734,184 | 3/1988 | Burleigh et al. | 204/411 |

FOREIGN PATENT DOCUMENTS 0022384 2/1983 Japan ................................. 204/267

OTHER PUBLICATIONS

Osswald et al., "Flow-Through System of High Stability for the Measurement of Ion Activities in Clinical Chemistry", Chimia 31 (1977).

Primary Examiner—Robert Raevis
Attorney, Agent, or Firm—Watson, Cole, Grindle & Watson

[57] ABSTRACT

An analyzing apparatus primarily designed for the analysis of body fluids, includes a feeding device, a measuring unit formed by a string of measuring cells linked by a channel, and a waste disposal unit for removal of the samples analyzed. Such an analyzing apparatus may be tailored to suit specific purposes by providing the measuring unit, or at least parts thereof, as modular units, which can directly be coupled to the feeding device and the waste disposal unit via a separate control block.

3 Claims, 2 Drawing Sheets

1

ANALYZING APPARATUS

This application is a continuation of Ser. No. 209,370 filed Jun. 21, 1988 (now abandoned).

BACKGROUND OF THE INVENTION

This invention relates to an analyzing apparatus primarily designed for the purpose of analyzing body fluids, comprising a feeding device, multiple-cell measuring device, to be called measuring unit in the following, which is constituted by a string of measuring cells linked by a channel, and a waste disposal unit for removal of the samples analyzed.

DESCRIPTION OF THE PRIOR ART

Conventional analyzing apparatuses of this kind usually are intended for a very limited range of application and may be used only for specific types of analyses. They are generally not suited for other applications.

SUMMARY OF THE INVENTION

It is an object of this invention to eliminate this disadvantage by proposing an analyzing apparatus of the above type which permits a greater variety of applications in a simple way.

In the invention this is achieved by configuring the measuring unit, or at least parts thereof, as a module which may be directly coupled to the feeding device and the waste disposal unit by means of a separate control block. The waste disposal unit may be provided with a rinsing unit, especially for cleaning the measuring cells and the channel linking them.

These measures will permit the analyzing apparatus to be extended by the addition of further modules containing further measuring units, which will also extend the range of applications of the apparatus.

For necessary sealing of the couplings of the individual modules the coupling parts may be provided with sealing rings with a square cross-section.

In a preferred variant of an analyzing apparatus described by the invention the module containing the measuring unit or parts thereof may be provided with a hose fitting connecting to the channel linking the measuring cells, which fitting has a cylindrical wall which is made from electrically insulating material and surrounds the hose that may be attached to the fitting.

In this way electrical leakage currents arising from the formation of liquid bridges between the outer surface of the fitting and the inner surface of the hose attached to the fitting are avoided; normally, such bridges result from samples and sample remnants eventually forming a leakage path towards a block containing the module, whose temperature usually is controlled by a heater unit and which is made from electrically conducting material, such as alumium or some other metal, in order to promote heat transfer onto the module. It is such leakage paths, however, which will affect the measuring process, above all, if electrochemical probes are employed. The formation of these paths is largely prevented by the cylindrical wall surrounding the hose fitting.

In order to permit a particularly simple method of cleaning, another feature of the invention provides that the module containing the measuring unit be provided with a valve controlling the channel linking the measuring cells on the inlet end, and that a bypass channel should branch off in front of the inlet of this valve. This will permit separate cleaning of the feeding device located in front of the measuring unit, before cleaning of the measuring unit proper, which will prevent any coagulates in the feeding device from being swept into the channel linking the measuring cells, whose cross-section usually is very small. Besides, the addition of a bypass channel will permit direct entrance of the samples to be analyzed into the measuring unit without using the feeding device.

Another feature of the invention provides branch-off channels leading from the channel linking the measuring cells to coupling parts of the module, to which coupling parts another module containing measuring cells and a channel linking these cells may be attached, which is preferably provided with a valve on its inlet end.

In this simple manner the measuring unit may be extended, which will enable the sample to be examined for a greater number of parameters, or the measuring unit may be doubled, which will permit the finding of deviations in the values obtained for one and the same sample, thus improving the accuracy of analysis From a design point of view it will be of advantage if the control block containing the valve and the bypass line is configured as a separate module.

In this way the control block, which is fairly complex to manufacture, may be coupled to various modules containing measuring units.

It may further be provided that the module containing the measuring unit be coupled to modular sensors, i.e., to ion-sensitive electrodes in particular.

This will permit easy adaptation of the analyzing apparatus to suit the desired purpose.

Another object of the invention is the configuration of an analyzing apparatus with a measuring unit permitting pH determination with the use of a reference electrode in addition to other measurements, such as determination of the gas content of a sample, in such a way as to prevent the sample to be analyzed from being affected by the electrolyte leaking from the reference electrode.

According to the invention this is achieved by positioning the measuring cell containing the reference electrode at the end of a stub channel branching off from the channel linking the measuring cells, the branch-off preferably being in vertical upwards direction.

By positioning the reference electrode externally, the sample contained in the channel linking the measuring cells is protected from contamination by the electrolyte leaking from the reference electrode. Moving the reference electrode to a position above the main channel is preferred as the cross-sections of the main channel and the stub channel usually are very small and the capillary effect will prevent the electrolyte from descending.

In an analyzing apparatus primarily designed for analyzing body fluids, comprising a feeding device, a measuring unit constituted by a string of measuring cells lined by a channel, and a waste disposal unit for removal of the samples analyzed, a further aspect of the invention provides that a bypass line should open into the channel linking the measuring cells between the feeding device and the nearest measuring cell following it, and that a valve be added between this opening and the nearest measuring cell, by means of which the channel linking the measuring cells can be blocked—the valve and the channel linking the measuring cells and the bypass line preferably being integrated in a module, and the bypass line ending in a fitting to which a hose or another module may be directly attached.

The bypass line is of advantage both for cleaning the apparatus and for feeding in the sample; for instance, a sample may be entered via the bypass line into the channel linking the measuring cells, i.e., by injection, without using the sample feeding device.

In order to be able to maintain prescribed sample temperature, a further feature of the invention provides that the modules be inserted into a block with thermostat control, which is preferably made from aluminium. By controlling the heater unit of this block a suitable temperature may be set.

DESCRIPTION OF THE DRAWINGS

Following is a more detailed description of the invention as illustrated by the attached drawings, in which.

DETAILED DESCRIPTION OF THE PREFERRED EMBODIMENTS

Figure 1:
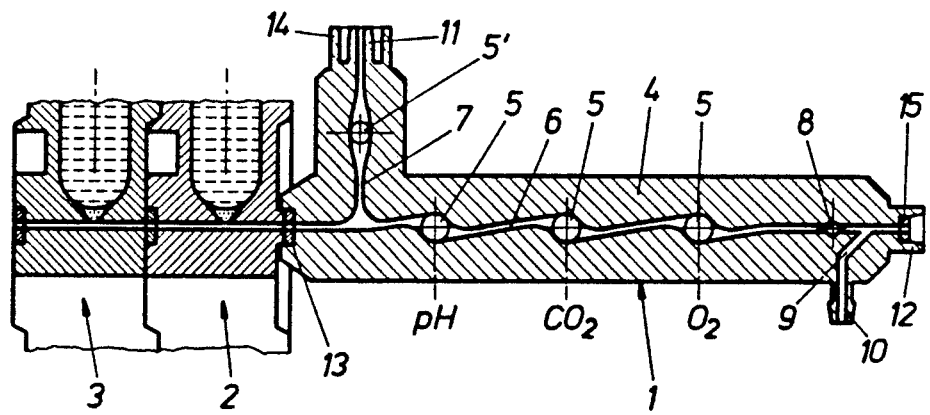
FIGS. 1 to 6 show different variants of measuring units of an analyzing apparatus as specified by the invention, FIG. 1 presenting an arrangement consisting of several modules 1 to 3.

Module 1 essentially consists of a unit 4 containing several measuring cells 5, 5', which are linked by a channel 6 and a stub channel 7 branching off therefrom. Channel 6 has a very small cross-section and is controlled by the valve 8. Valve 8 is located between the sample entrance opening and the nearest measuring cell 5.

In the part of the channel 6 between the sample entrance opening and the valve 8 there is a branch-off, i.e., a bypass line 9, ending in a fitting 10 to which may be directly attached a hose, leading for instance to a waste or overflow container, preferably via a valve, or a hose, the inlet end of which may be provided with a valve. The addition of such a valve will permit direct injection of the sample into the channel linking the measuring cells, without any undesirable pressure rise in the measuring cells 5, 5', as the sample excess may be drained through the open valve into the overflow container.

The stub channel 7 linking a cell 5' containing the reference electrode for pH measurement to the rest of channel 6 leads to a fitting 11 to which may be attached a further module if desired, or which may be sealed with a suitable cap.

Channel 6 opens tangentially into the individual measuring cells 5, 5', the feeding section of the channel entering the lower region of each cell and the draining section leaving the upper region of each cell. By guiding the channel 6 in this way any air bubbles contained in the sample will be carried off by the sample itself as it enters the measuring cells, or they are at least prevented from remaining in the immediate vicinity of the sensitive tip of the probe inserted into the measuring cell, which will help avoid errors of measurement.

The ends of the unit 4 configured as module 1, through which the channel 6 passes, are provided with couplings 12, 13, which will establish a connection to the feeding device not shown here, or to an electrode unit also configured as a module 2. As is shown in FIG. 1, another electrode unit configured as a module 3 may be attached to module 2.

These modules are preferably integrated in a thermostat-controlled block (not shown), which is preferably made from aluminium and is provided with a controlled heating unit.

The fittings 11 are surrounded by a cylindrical wall 14, which will prevent leakage currents from forming between the sample and the module block usually characterized by electrical conductivity; leakage paths may be established along sample remnants between the outer surface of the fitting 11 and the inner surface of the hose attached to the fitting, which may contaminate the environment of the fitting 11 and may form conductive bridges onto the block containing the individual modules (not shown).

For proper sealing of the couplings of the individual modules, sealing rings 15 with a square cross-section are provided, which are made from a soft plastic material and will leave open only the cross-section of channel 6 and the stub channel 7.

In the analyzing apparatus shown in FIG. 1 probes are inserted into the measuring cells 5 of the module 1 for determination of the $O_2$ and $CO_2$ contents or the pH value. The modules 2 and 3 coupled to this module 1 are intended for measuring the concentrations of certain ions.

Figure 2:
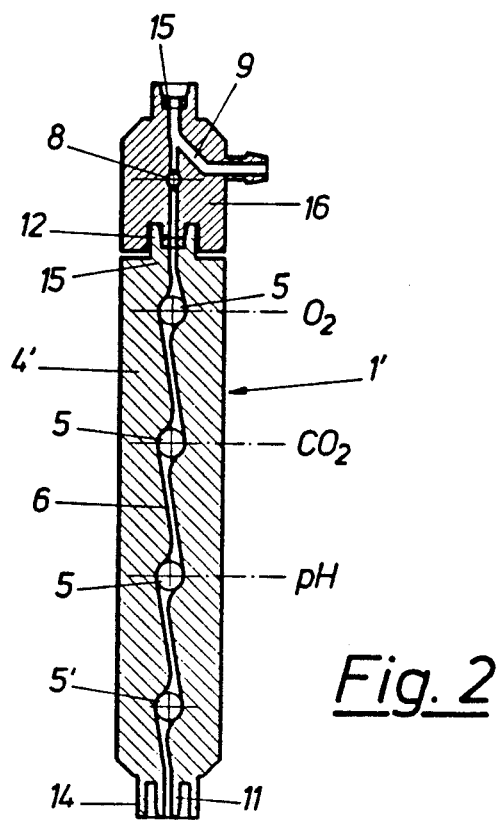

In the variant shown in FIG. 2 the unit 4' only comprises a channel 6 passing through its entire length, which links the measuring cells 5, 5' and ends in a fitting 11. This unit 4', which constitutes the module 1', is connected to a module 16 via a coupling part 12 provided with a square sealing ring 15, which module 16 is added between the feeding device (not shown here) and the unit 4', and contains the valve 8 and the bypass line 9.

Figure 3:
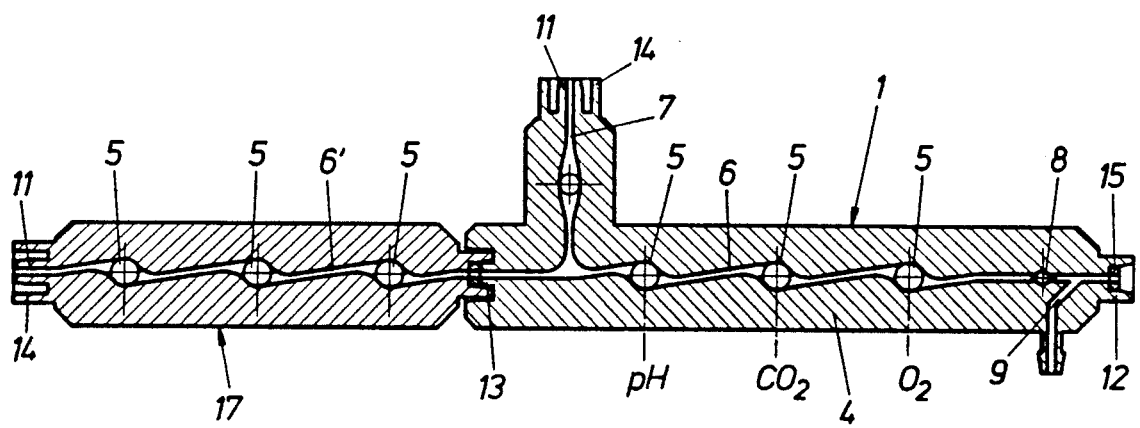

In the variant according to FIG. 3 the module 1 is coupled to yet another module 17 containing further measuring cells 5 and a channel 6' linking these cells, which channel 6' ends in a fitting 11 surrounded by a cylindrical wall 14. With this variant two measuring units are obtained in tandem arrangement, module 1 being provided with a male/female pair of couplings 12, 13, i.e., one on each end.

Figure 4:
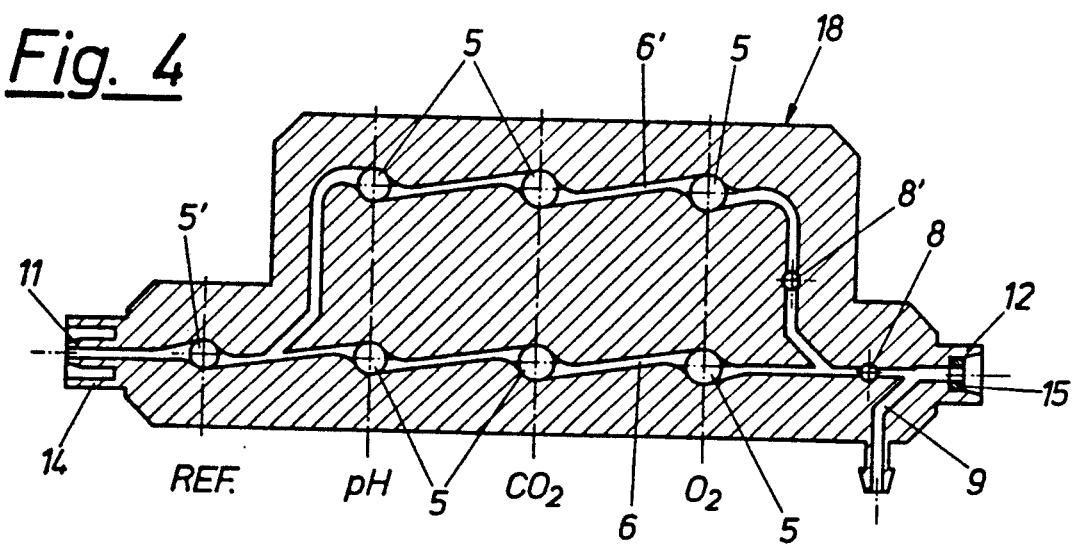

FIG. 4 presents a module 18 containing two parallel measuring units, valve 8 controlling both channels 6, 6', and valve 8' only channel 61. Channel 6' branches off from channel 6 between valve 8 and the measuring cell of channel 6 next to the inlet, and meets channel 6 again immediately in front of the measuring cell 5' containing the reference electrode for pH measurement. Module 18 thus is designed like module 1' in FIG. 2, with the addition of the parallel measuring unit.

Figure 5:
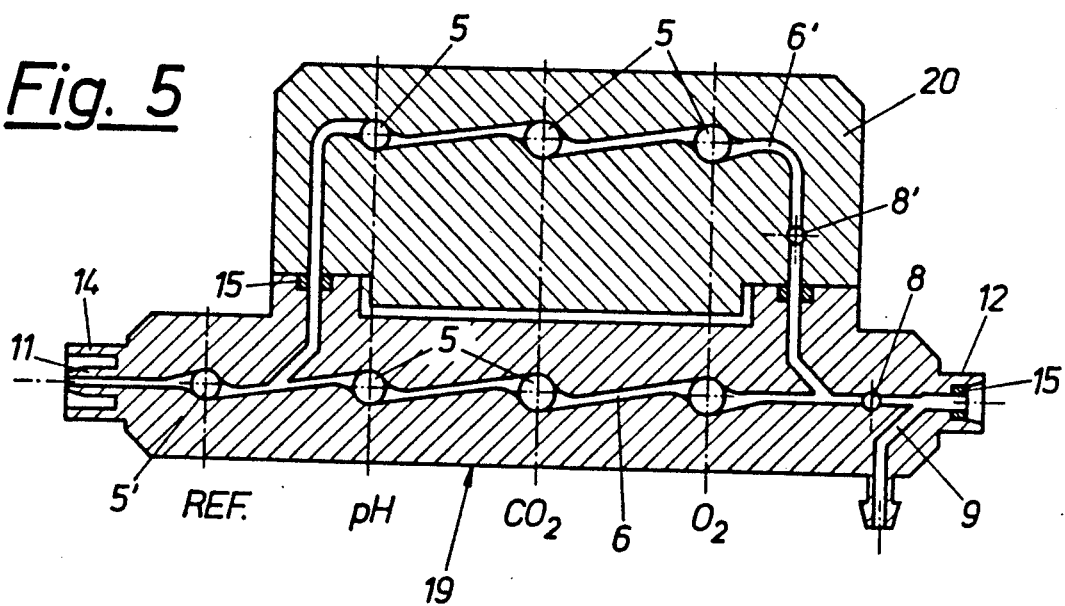

The variant shown in FIG. 5 differs from that in FIG. 4 in so far as the parallel measuring unit carrying the valve 8' controlling channel 6' is placed in a separate module 20 in this instance.

Module 19, which essentially corresponds to module 1', differing from the latter only by the channel sections 6' branching off from channel 6, is coupled to module 20 via square rings 15.

Figure 6:
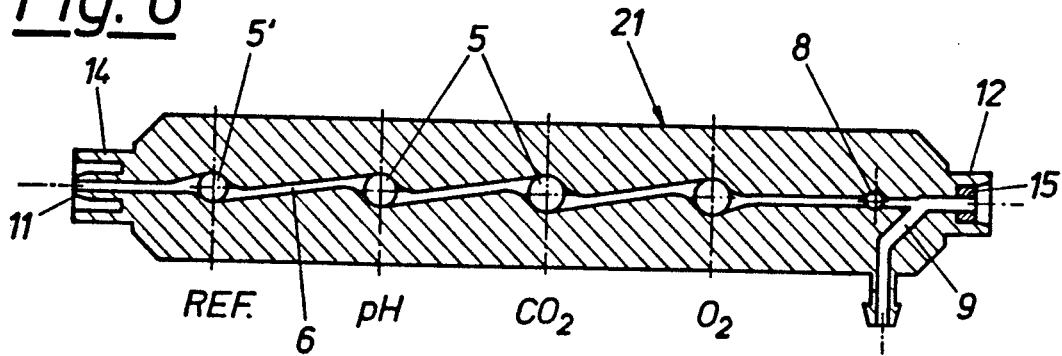

The module 21 presented in FIG. 6 essentially corresponds to module 1' in FIG. 2, apart from the fact that in module 21 the valve 8 and the bypass line 9 are integrated additionally.

We claim:

1. A module for use in an analyzing apparatus, said module comprising an inlet opening, a primary outlet opening, a secondary outlet opening and a non-linear primary flow channel extending from said inlet opening to said primary outlet opening, said primary flow channel tangentially opening into and exiting from a plurality of primary cells, said primary cells receiving electrochemical measuring electrodes for measuring characteristics of a sample fluid in said primary flow channel, and a secondary flow channel which is connected to said primary flow channel and which branches off from said primary flow channel to said secondary outlet opening, said secondary flow channel defining a secondary cell for receiving a reference electrode.

2. A module according to claim 1, including a valve in said primary flow channel between a first of said primary cells and said inlet opening.

3. A module according to claim 2, including a tertiary outlet opening and a tertiary flow channel connected to said primary flow channel between said valve and said inlet opening and which branches off from said primary flow channel and communicates with said tertiary outlet opening.

* * * * *